(12) United States Patent
Bicknell et al.

(10) Patent No.: US 7,938,802 B2
(45) Date of Patent: May 10, 2011

(54) AUTOMATIC INJECTION DEVICES

(75) Inventors: Stephen Bicknell, Warwickshire (GB); Joseph F. Julian, Libertyville, IL (US); William L. Rudzena, Johnsburg, IL (US)

(73) Assignee: Abbott Biotechnology Ltd., Hamilton (BM)

( * ) Notice: Subject to any disclaimer, the term of this patent is extended or adjusted under 35 U.S.C. 154(b) by 272 days.

(21) Appl. No.: 11/630,507

(22) PCT Filed: Jun. 23, 2005

(86) PCT No.: PCT/GB2005/002487
§ 371 (c)(1),
(2), (4) Date: Jan. 7, 2008

(87) PCT Pub. No.: WO2006/000785
PCT Pub. Date: Jan. 5, 2006

(65) Prior Publication Data
US 2008/0208125 A1 Aug. 28, 2008

(30) Foreign Application Priority Data
Jun. 23, 2004 (GB) .................... 0414054.7

(51) Int. Cl.
*A61M 5/20* (2006.01)
(52) U.S. Cl. ........................................ 604/135; 604/157
(58) Field of Classification Search .................. 604/135, 604/165.03
See application file for complete search history.

(56) References Cited

U.S. PATENT DOCUMENTS

| | | | |
|---|---|---|---|
| 2,888,924 A | 6/1956 | Dunmire | |
| 3,742,948 A | 7/1973 | Post et al. | |
| 3,797,489 A | 3/1974 | Sarnoff | |
| 4,929,237 A | 5/1990 | Medway | |
| 4,955,868 A | 9/1990 | Klein | |
| 5,049,133 A | 9/1991 | Villen Pascual | |
| 5,163,918 A | 11/1992 | Righi | |
| 5,267,972 A | 12/1993 | Anderson | |
| 5,295,975 A | 3/1994 | Lockwood | |
| 5,298,024 A | 3/1994 | Richmond | |
| 5,300,030 A * | 4/1994 | Crossman et al. | 604/136 |
| 5,346,480 A | 9/1994 | Hess | |
| 5,376,080 A | 12/1994 | Petrussa | |
| 5,433,712 A | 7/1995 | Stiles | |

(Continued)

FOREIGN PATENT DOCUMENTS

EP 1364667 11/2003
(Continued)

OTHER PUBLICATIONS

International Search Report for Application No. PCT/US07/15095, dated Sep. 11, 2008.
(Continued)

*Primary Examiner* — Nicholas D Lucchesi
*Assistant Examiner* — Diva Ranade
(74) *Attorney, Agent, or Firm* — McCarter & English, LLP

(57) ABSTRACT

An injection device comprises a syringe (1) extendible against a spring bias (9) from a retracted position in a housing (2) to a projecting injecting position. A spring biased plunger has collapsible elbows (10) which, when the plunger is released, initially engage the end of the syringe to drive it to the projecting position, whereupon arresting of the syringe movement causes the elbows to collapse inside the syringe to allow the plunger to engage and drive the bung (3).

14 Claims, 1 Drawing Sheet

U.S. PATENT DOCUMENTS

Figure 1:
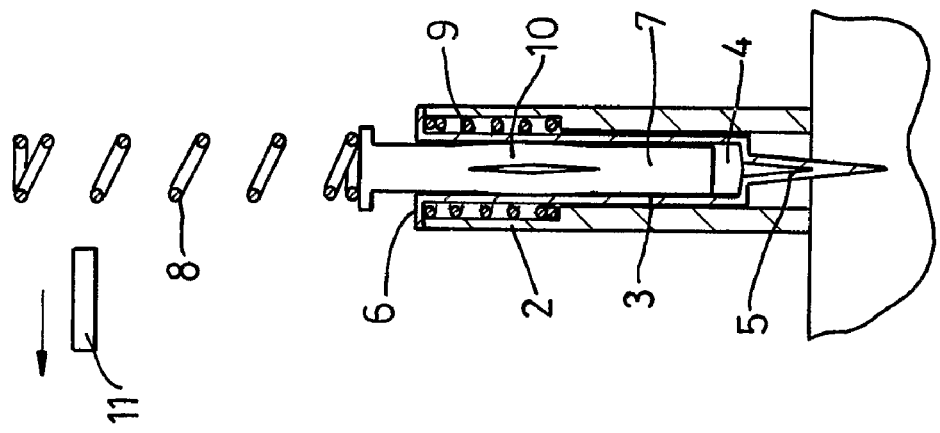

| | | | | |
|---|---|---|---|---|
| 5,620,421 | A * | 4/1997 | Schmitz | 604/135 |
| 5,658,259 | A | 8/1997 | Pearson | |
| 6,213,987 | B1 | 4/2001 | Hirsch | |
| 6,319,233 | B1 | 11/2001 | Jansen | |
| 6,319,234 | B1 | 11/2001 | Restelli | |
| 6,322,540 | B1 | 11/2001 | Grabis | |
| 6,475,194 | B2 | 11/2002 | Domici | |
| 6,712,788 | B2 | 3/2004 | Righi | |
| 6,752,798 | B2 | 6/2004 | McWethy | |
| 6,773,415 | B2 | 8/2004 | Heiniger | |
| 6,805,686 | B1 * | 10/2004 | Fathallah et al. | 604/135 |
| 6,808,507 | B2 | 10/2004 | Roser | |
| 6,817,989 | B2 | 11/2004 | Svendsen | |
| 6,926,697 | B2 | 8/2005 | Malenchek | |
| 6,945,960 | B2 | 9/2005 | Barker | |
| 6,976,976 | B2 | 12/2005 | Doyle | |
| 6,986,760 | B2 | 1/2006 | Giambattista | |
| 7,004,929 | B2 | 2/2006 | McWethy | |
| 7,056,306 | B1 | 6/2006 | Halseth | |
| 7,320,682 | B2 | 1/2008 | Cocker | |
| 7,361,160 | B2 | 4/2008 | Hommann | |
| 7,497,847 | B2 | 3/2009 | Crawford | |
| 2001/0005781 | A1 | 6/2001 | Bergens et al. | |
| 2003/0187401 | A1 | 10/2003 | Doyle | |
| 2004/0024367 | A1 | 2/2004 | Gilbert | |
| 2004/0054327 | A1 * | 3/2004 | Gillespie, III | 604/135 |
| 2004/0229854 | A1 | 11/2004 | Haan De | |
| 2005/0020979 | A1 | 1/2005 | Westbye et al. | |
| 2005/0090647 | A1 | 4/2005 | Gatanaga et al. | |
| 2005/0095208 | A1 | 5/2005 | Battaglia et al. | |
| 2005/0096597 | A1 | 5/2005 | Crawford | |
| 2005/0137196 | A1 | 6/2005 | Timmer et al. | |
| 2005/0273061 | A1 | 12/2005 | Hommann et al. | |
| 2006/0140907 | A1 | 6/2006 | Blumberg et al. | |
| 2006/0167413 | A1 | 7/2006 | Marshall et al. | |
| 2006/0189933 | A1 | 8/2006 | Alheidt | |
| 2006/0253083 | A1 * | 11/2006 | Liu | 604/198 |
| 2007/0129674 | A1 | 6/2007 | Liversidge | |
| 2007/0142776 | A9 * | 6/2007 | Kovelman et al. | 604/136 |
| 2007/0239117 | A1 | 10/2007 | Chelak | |
| 2008/0097337 | A1 | 4/2008 | Judd | |
| 2008/0208125 | A1 | 8/2008 | Bicknell et al. | |
| 2008/0208140 | A1 | 8/2008 | Barrelle | |
| 2008/0269692 | A1 | 10/2008 | James | |
| 2008/0300549 | A1 | 12/2008 | Verespej | |
| 2009/0024093 | A1 | 1/2009 | Carrel | |
| 2009/0157012 | A1 | 6/2009 | Magne | |
| 2009/0240210 | A1 | 9/2009 | Walton | |

FOREIGN PATENT DOCUMENTS

| | | |
|---|---|---|
| EP | 2085104 A1 | 8/2009 |
| GB | 2243552 A | 11/1991 |
| GB | 2388033 | 11/2003 |
| JP | 50-14835 | 5/1975 |
| JP | 5-161712 | 6/1993 |
| WO | WO 97/29131 | 8/1997 |
| WO | WO 02/12502 | 2/2002 |
| WO | WO 2004/000397 | 12/2003 |
| WO | WO 2004000397 * | 12/2003 |
| WO | 2005/002653 | 1/2005 |
| WO | WO 2005/002653 | 1/2005 |
| WO | WO 2006/000785 | 1/2006 |
| WO | WO 2008/005315 | 1/2008 |

OTHER PUBLICATIONS

BD Preventis™, Shielding System for Prefilled Syringes, http://www.bd.com/pharmaceuticals/products/safety-engineered.asp, last accessed on Aug. 26, 2010.

Examination Report for New Zealand Application No. 552340, dated Apr. 27, 2009.

Inquiry issued by the Russia Federal Intellectual Property Institute on Russian Patent Application No. 2006145501/14(049694), dated May 21, 2009.

International Search Report on International Patent Application No. PCT/GB2005/002487, dated Aug. 19, 2005.

International Preliminary Report on Patentability on International Patent Application No. PCT/GB2005/002487, dated Sep. 7, 2006.

Notice of Reasons for Rejection issued by the Japanese Patent Office on Japanese Patent Application No. 2007-517459, dated Aug. 24, 2010.

Office Action issued by the Mexican Patent Office on Mexican Patent Application No. PA/a/2006/015056, dated Jul. 28, 2010, with English translation.

Notification of Reexamination issued by the Chinese Patent Office on Chinese Patent Application No. 200580020958.6, dated Aug. 17, 2010.

Rejection Decision issued by the Chinese Patent Office on Chinese Patent Application No. 200580020958.6, dated Jun. 5, 2009.

First Office Action issued by the Chinese Patent Office on Chinese Patent Application No. 200580020958.6, dated Sep. 5, 2008.

Examiner's First Report issued by the Australian Patent Office on Australian Patent Application No. 2005256832, dated Feb. 22, 2010.

Communication pursuant to Article 94(3) EPC issued by the European Patent Office on European Patent Application No. 05 758 156.3-2320 dated Jan. 18, 2011.

* cited by examiner

AUTOMATIC INJECTION DEVICES

There are various forms of automatic injection device which when operated cause the needle of a syringe to be moved forwardly so that it projects from a protective housing prior to actuation of the syringe to express a dose of liquid through the needle. It is important to try to ensure that the syringe is moved bodily forward to expose the needle before the liquid charge is pressurised so that dribbling from the needle does not occur before the actual injection takes place. It is an object of this invention to provide a mechanism which operates in this desired manner.

According to the invention there is provided an injection device for causing a dose of liquid to be ejected from the needle at one end of a syringe located within a housing of the device, the syringe being movable by a plunger, upon release of an actuating bias member at one end of the housing, to move the syringe, from a first position wherein the needle is shrouded by the housing, to a second position wherein the needle projects from the other end of the housing, the plunger being in the form of a rod with a longitudinally centrally located flexible projecting portion which, prior to release of said actuating bias member, is situated beyond the other end of the syringe, such that a primary movement of the plunger, under the bias of the actuating bias member, will cause the projecting portion to bear against the other end of the syringe such that the syringe is moved from said first to said second position, whereupon arresting of further movement of the syringe, results in the flexible portion collapsing inwardly so that it enters the syringe, thus enabling the plunger to move by a secondary movement, within the syringe, into contact with and to act upon a plug to compress the liquid within the syringe and cause expression of the liquid through the syringe needle.

With such an arrangement, the projecting portion will remain in its projecting position (in order to move the syringe from the first to the second position) until the force increases to such an extent which allows the projecting portion to collapse inwardly so that the plunger can then move within the syringe to cause the liquid to be expressed through the syringe.

The projecting portion can comprise one or more flexible elbows projecting beyond the normal circumference of the rod, but compressible into said circumference. This could be in the form of two elbows defined either side of a longitudinal slit in the rod. The elbows could be pre-formed as a pair of arms either side of the longitudinal slit between upper and lower solid portions of the rod.

Preferably the injection device will contain a return bias member acting between the syringe housing and the other end of the syringe to hold the syringe retracted within the housing until the actuating bias member is released.

One or more of the bias members provided within the housing can be in the form of a coil spring.

Figure 2:
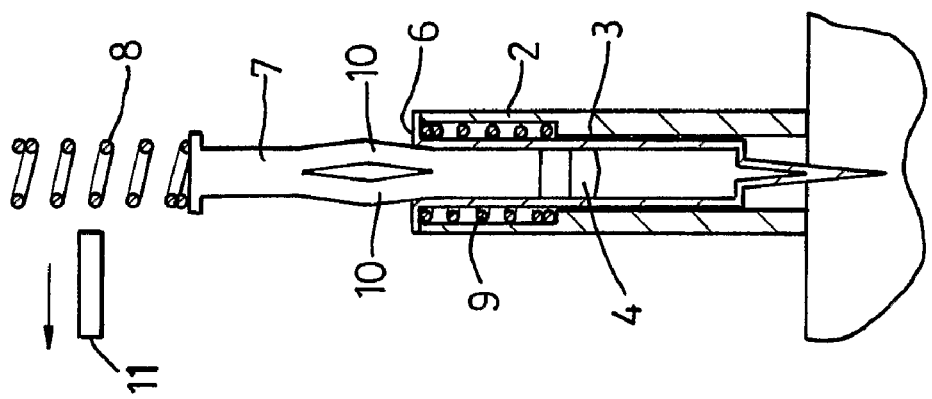
Figure 3:
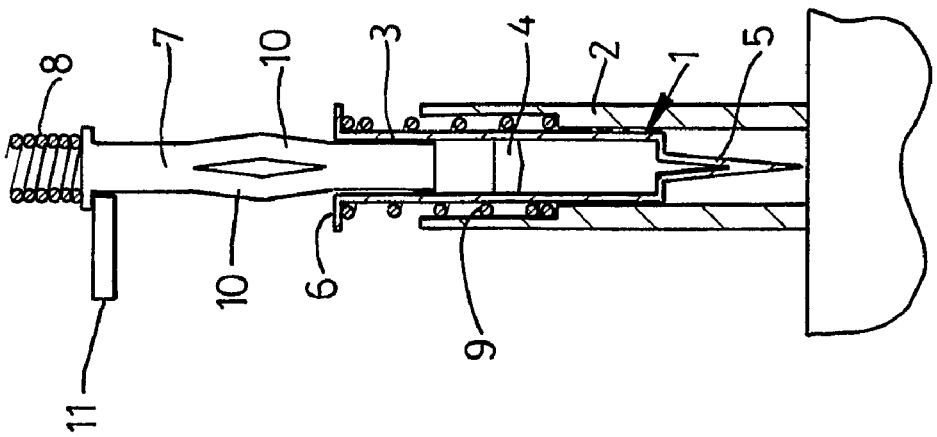

The invention may be performed in various ways and a preferred example thereof will now be described, with reference to the accompanying diagrammatic drawings, in which:

FIG. 1 FIG. 1 is a sectional view through an injection device of this invention prior to use; and FIGS. 2 and 3 are similar views showing successive stages of operation of the injection member.

The injection device shown in the drawings comprises a syringe 1 located within a protective housing 2. The syringe comprises a 3 incorporating a liquid dose held in place by a bung 4 and having a needle 5 through which the dose can be ejected by applying pressure to the bung 4. The 3 has an enlarged head 6. A plunger 7 is biased forwardly by a coil spring 8, but is held back in a latched position (FIG. 1) until such time as a trigger shown schematically at 11 is actuated to release the plunger and the spring 8. Prior to use the syringe 1 is held retracted in the housing 2 by a coil spring 9.

It will be seen that the plunger 7 is in the form of a rod having a central portion which defines a pair of projecting elbows 10. These can be pre-formed as part of a moulded plunger 7. The projecting elbow portions 10 are flexible so that they can be moved inwardly to cause that portion of the rod to adopt a circumference similar to that of the rest of the rod. As can be seen in FIG. 2, when the plunger is released and biased by the spring 8 the expanded region formed by the elbows 10 rests against the head 6 of the 3 and the force provided is sufficient to compress the spring 9 until such time as the head 6 abuts the top of the housing 2, whereupon further movement of the 3 is arrested. The continual bias created by the spring 8 then causes the elbows 10 to be compressed inwardly as they enter into the interior of the 3. With the elbows 10 in the collapsed state, the plunger can then move relatively easily within the 3 so as to act upon the bung 4 and thus cause the contents of the syringe to be ejected through the needle 5.

The illustrated configuration of the plunger 7 provides several technical advantages. It can be moulded integrally. Also the collapsing movement of the projecting elbows provides an arrangement which can provide a suitable injection force to cause the needle to enter the skin to a suitable depth, but then provide a relatively low drag against the inner wall of the syringe container so that the major portion of the thrust of the spring for the remainder of its stroke is applied to the bung 4. It will be appreciated that other configurations of collapsing projection could be used in place of the collapsing elbows.

The invention claimed is:

1. An injection device for causing a dose of liquid to be ejected from a needle (5) at a distal end of a syringe (1) located within a housing (2) of the device, the syringe containing a moveable bung (4) and the syringe being movable relative to the housing by a plunger (7), whereupon release of an actuating bias member (8) at a proximal end of the housing moves the syringe from a first position relative to the housing wherein the needle is shrouded by the housing, to a second position relative to the housing wherein the needle projects from a distal end of the housing, the plunger being in the form of a rod with a flexible projecting portion (10) which, prior to release of said actuating bias member, is situated rearwardly of the proximal end of the syringe, such that a primary movement of the plunger, under the bias of the actuating bias member, causes the projecting portion to bear against the proximal end of the syringe such that the syringe is moved from said first to said second position, whereupon arresting of further movement of the syringe, results in the flexible projecting portion collapsing inwardly so that it enters the syringe, thus enabling the plunger to move forwardly within the syringe, to act upon said bung to compress the liquid within the syringe and cause expulsion of the liquid through the syringe needle.

2. The injection device as claimed in claim 1, wherein the projecting portion (10) comprises a flexible elbow projecting beyond the normal circumference of the rod, but compressible into said circumference.

3. The injection device as claimed in claim 2, wherein an elbow (10) is defined on either side of a void in the rod.

4. The injection device as claimed in claim 3, wherein the elbows are preformed as a pair of arms (10) on either side of the void between spaced front and rear solid portions of the rod.

5. The injection device as claimed in claim 1, including a return bias member (9) acting between the syringe housing and the distal end of the syringe to hold the syringe retracted within the housing until the actuating bias member is released.

6. The injection device as claimed in claim 5, wherein one or more of the bias members provided within the housing is in the form of a coil spring.

7. The injection device as claimed in claim 1, wherein the housing is fixed relative to the syringe.

8. An injection device comprising:
a housing (2);
a syringe (1) slideably mounted within said housing for movement between a shrouded retracted position relative to the housing and an extended injecting position relative to the housing;
a bung (4) slideably mounted in said syringe and moveable to expel a liquid dose through a needle (5) at the distal end of the syringe;
a plunger (7) having an end operable to move said bung (4) and to transmit an expulsion force thereto; and
a bias spring (8) operable to move said plunger from a first position to a second position,
wherein said plunger is provided with projecting regions (10) which are outside said syringe when said plunger is at its first position but which in use, on movement away from said first position, engage a proximal end (6) of said syringe to drive the syringe to its extended injecting position relative to the housing, whereupon arresting of further movement of said syringe causes said projecting regions to collapse inwardly so that they enter the syringe to allow said plunger to expel a liquid dose.

9. The injection device as claimed in claim 8, wherein an elbow (10) is defined on either side of a void in the rod.

10. The injection device as claimed in claim 9, wherein each of the elbows are preformed as an arm (10) on either side of the void between spaced front and rear solid portions of the rod.

11. The injection device as claimed in claim 8, including a return bias member (9) acting between the syringe housing and the distal end of the syringe to hold the syringe retracted within the housing until the actuating bias member is released.

12. The injection device as claimed in claim 9, including a return bias member (9) acting between the syringe housing and the distal end of the syringe to hold the syringe retracted within the housing until the actuating bias member is released.

13. The injection device as claimed in claim 10, including a return bias member (9) acting between the syringe housing and the distal end of the syringe to hold the syringe retracted within the housing until the actuating bias member is released.

14. The injection device as claimed in claim 8, wherein the housing is fixed relative to the syringe.

\* \* \* \* \*